United States Patent
Wiley, Sr.

(10) Patent No.: US 9,086,359 B2
(45) Date of Patent: Jul. 21, 2015

(54) METHOD FOR DETECTING OIL AND GAS FROM THE SURFACE BY NUCLEAR MAGNETIC RESONANCE IMAGING

(75) Inventor: Thomas J. Wiley, Sr., Florissant, MO (US)

(73) Assignee: NUMATEX, INC., Dixon, KY (US)

( * ) Notice: Subject to any disclaimer, the term of this patent is extended or adjusted under 35 U.S.C. 154(b) by 843 days.

(21) Appl. No.: 13/362,070

(22) Filed: Jan. 31, 2012

(65) Prior Publication Data
US 2013/0193964 A1    Aug. 1, 2013

(51) Int. Cl.
*G01V 3/00* (2006.01)
*G01N 24/08* (2006.01)
*G01V 3/14* (2006.01)

(52) U.S. Cl.
CPC .............. *G01N 24/081* (2013.01); *G01V 3/14* (2013.01)

(58) Field of Classification Search
CPC ........................................................ G01V 3/14
USPC ................................. 324/303, 300
See application file for complete search history.

(56) References Cited

U.S. PATENT DOCUMENTS

| | | | | |
|---|---|---|---|---|
| 7,825,659 B2* | 11/2010 | Georgi et al. | ................ | 324/303 |
| 8,248,067 B2* | 8/2012 | Ong | ............................... | 324/303 |
| 8,400,147 B2* | 3/2013 | Anand et al. | .................. | 324/303 |
| 8,736,269 B2* | 5/2014 | Sudow et al. | ................. | 324/337 |

* cited by examiner

*Primary Examiner* — Louis Arana
(74) *Attorney, Agent, or Firm* — C. Richard Martin

(57) ABSTRACT

A process using Nuclear Magnetic Resonance (NMR) with pre-determined oil specimens at the earth's surface by which to match the location and lateral boundaries of any and every producible oil reservoir responsive to NMR technology, to provide estimates to useable industry standards of porosity and permeability of said reservoirs for exploration purposes by NMR, to detect and identify depth and direction of faults in any given oil area by NMR, to provide mapping of surveyed areas prior to drilling either offset or wildcat ventures resulting from NMR testing, to evaluate reservoir and production potential in existing oil fields by NMR, to detect the existence of natural gas by NMR, and the ability to condemn any proposed drilling location in view of failure.

15 Claims, 5 Drawing Sheets

METHOD FOR DETECTING OIL AND GAS FROM THE SURFACE BY NUCLEAR MAGNETIC RESONANCE IMAGING

FIELD OF THE INVENTION

The invention relates to the use of nuclear magnetic resonance imaging for detecting formations in the earth from the surface and specifically relates to detecting specific oil and gas reservoirs and faults in the earth and differentiating these reservoirs from free radicals.

BACKGROUND OF THE INVENTION

Nuclear Magnetic Resonance (NMR) is a phenomenon which occurs when nuclei of certain atoms, molecules, and/or molecular compounds are exposed to a second oscillating field at vector, resulting in measurable quantum properties of the subject(s) being introduced to said field.

NMR technology has advanced beyond theory and laboratory analysis to applications in medical science by which to determine and measure molecular displacement in the human body.

NMR has also been applied to the examination of earth substances for identity and source, with application to environmental issues.

In the field of petroleum, NMR has been applied mainly to techniques for down hole logging of oil wells in view of determining properties of live oil and wettability of oil formations after drilling, both by processes involving extraction of fluids from bore holes, and generating pulses from bore holes measured with antennae after the expense of drilling, dismissing the predictive powers of other crude specimens at the locations or in the drilled field.

No proponent has ever advanced a body of theory or methodology by which to detect oil or gas from the surface by NMR in view of drilling to a predicted target, nor to exercise mobility to examine remaining reservoir qualities from the surface by NMR, nor to identify, determine depths, or map faults in a given area by NMR, nor to use NMR as a tool to condemn non-bearing hydrocarbon areas.

SUMMARY OF THE INVENTION

The present invention provides a method for detecting subterranean reservoirs of oil and/or gas comprising the steps of obtaining a specimen of oil having a known composition of elements and compounds; providing a standardized NMR apparatus having a standardized cell; introducing a molecular amount of said specimen in said standardized cell; orienting the standardized cell proximal and perpendicular to the earth; scanning at or near the surface of the earth with said standardized cell containing said specimen until said standardized cell precesses; assigning test values upon which to evaluate the precession of the standardized cell; and determining the presence or absence of oil in the ground based on said assigned test values and the precession of the standardized cell.

The method may further comprise the step of obtaining a nuclear magnetic fingerprint of the specimen by analyzing the specimen by molecular fluid property analysis, such as gas chromatography and/or mass selection. The step of obtaining a specimen of oil may include obtaining a plurality of oil specimens from a plurality of oil reservoirs.

The step of assigning test values includes the steps of: assigning an energy level value based on a reflection of spin lattice activity in observation of magnetic force; assigning a Larmor strength value based on the level of matching molecular activity at vortex; assigning a porosity potential as a gauge of porosity in the earth based on fluid concentrations generating greater or lesser magnetic activity; and assigning a permeability potential based on oil saturation and comparative permeabilities within the area and as factored by informed geological realities within the area. The step of determining the presence or absence of oil comprises comparison of the energy level value, Larmor strength value, porosity potential and permeability potential. The method may further comprise the step of determining the presence of free radicals in the earth. The presence of free radicals is determined by high energy level readings.

The method further comprising the step of detecting and locating all faults as to width and depth associated within the test area. The step of detecting and locating all faults comprises the step of observing inverse oscillation of the standardized cell containing the oil specimen as it is passed over the earth. The step of detecting and locating all faults may be repeated using a plurality of oil specimens from a plurality of oil reservoirs.

The method may further include the step of mapping the acquired lateral boundaries, porosity, and permeability responses to NMR testing in all areas of the geological source of the specimen; recommending ultimate drilling locations for ultimate recovery of oil; and condemning all areas associated with faults, non-NMR response, and the hyper activity of free radicals.

Fluid specimens of live crude oil and/or residual oil derived from select locations are subjected to molecular identity, sorting out the mixtures of linear, branched, cyclic and aromatic compounds found in each specimen derived by gas chromatograph analysis with a mass selective detector. A broad variety of specimens are inserted into vials and subjected to NMR testing processes for vortex of their corresponding earth source at any depth until Larmor frequency is obtained. At various polar alignments, the absolute presence of corresponding reservoirs is detected and identified, with mobile vectoring that determines the depositional width and breadth of corresponding reservoirs, apex of each reservoir, and the porosity and permeability potential of each petroleum-bearing reservoir based on geological knowns within the area. Non-corresponding petroleum compounds will not precess to one another, while corresponding compounds precess absolutely without any interference from varieties of ground sediment, minerals, fluids, gases, and without confusion with any other applied specimen, all in view of determining ultimate oil and gas drilling potential. Existing oil fields can likewise be examined by NMR by which to gauge their remaining life, proximity to oil/water contact zones, and to recommend either additional recovery efforts, deepening, or plugging. However, free radical anomalies can occur in any given area, which may confuse even the operator most skilled in the art, but such free radicals in no way reduce the revealing properties of producible oil and gas reservoirs. Inverse precession reveals the existence and depth of any and every fault in the area, identifies their depth and direction, thus adding to the interpretive capabilities of petroleum deposition. Absence of all NMR specimen field applications leads to the condemnation of any given property for exploration potential.

These and other objects, features and advantages of the present invention will become apparent with reference to the text and the drawings of this application.

DETAILED DESCRIPTION OF PREFERRED EMBODIMENTS

Figure 1:
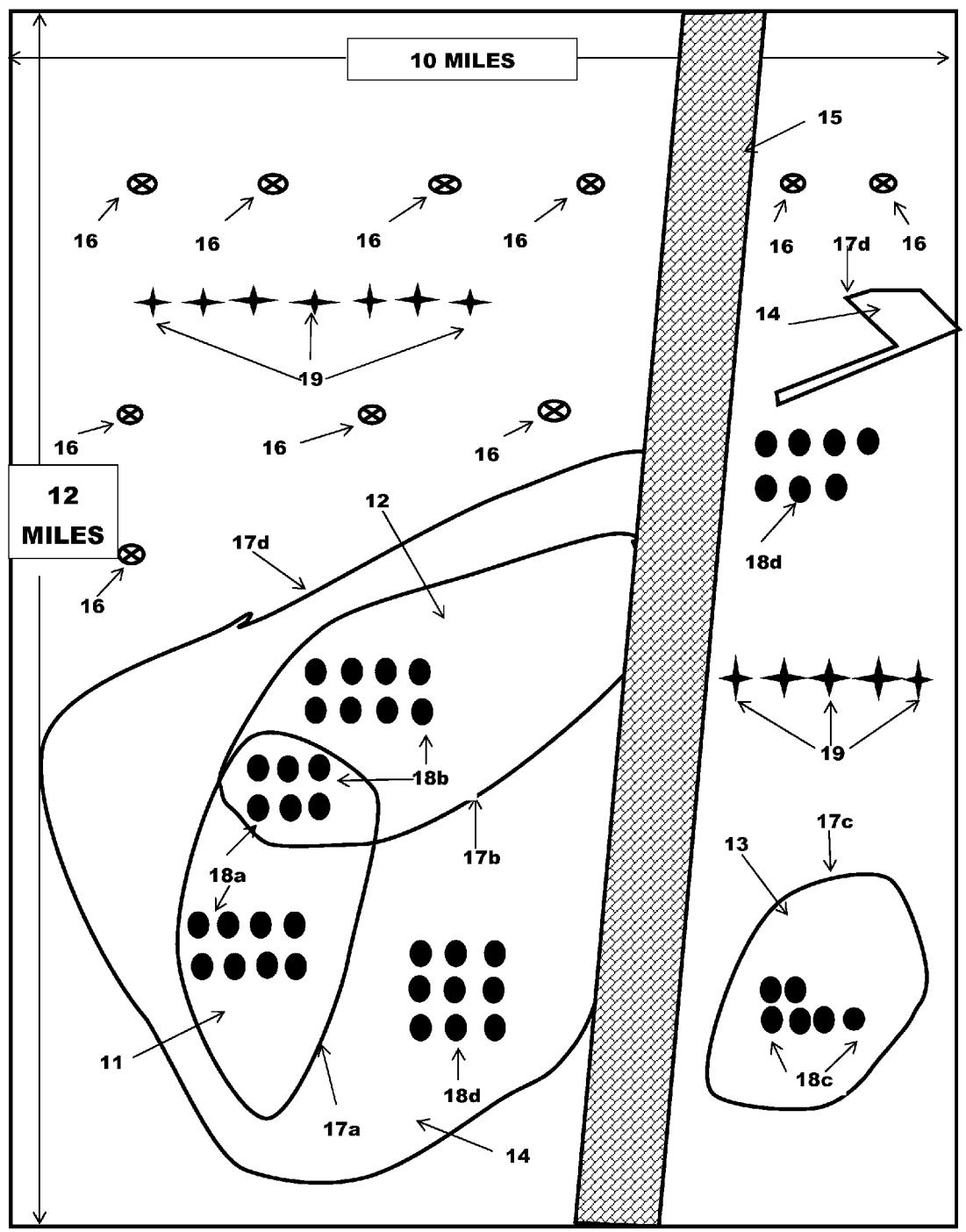
FIG. 1 is a top view in sectional elevation illustrating a first hypothetical oil and/or gas production area including indigenous deposition of specimens A, B, C and D, a fault line, and free radical data points, representative of geological conditions which occur worldwide.

It is to be understood that the following disclosures provide many hypothetical situations based on thousands of hydrocarbon combinations of bonded aromatic, linear, branched, and cyclic molecular compounds which are deposited in thousands of various oil formations all over the world in thousands of fickle geological conditions. The following disclosures, therefore, are not intended to be limited to the condensed examples and illustrations.

The present disclosure provides four analyzed oil compounds from various earth depths, vertical and horizontal schematics illustrating hypothetical test plots, incremental NMR test results, and hypothetical fault detection. In accordance with industry standards, various features are not drawn to scale, and geological features are simplified for understanding. Tables 1, 2, 3, and 4 below are four actual petroleum specimens, representative of varying hydrocarbon compounds found in thousands of oil formations around the world. For purposes of this disclosure, they are labeled A, B, C, and D within the schematic drawings and can be representative of any specimen from any depth.

TABLE 1

CRUDE SPECIMEN A

| COMPOUND | MOLECULAR FORMULA | APPROXIMATE % OF SPECIMEN |
|---|---|---|
| METHYLCYCLOHEXANE | C7H14 | 0.62 |
| HEPTANE | C7H16 | 0.19 |
| 1,3-DIMETHYL-BENZENE and/or 1,4-DIMETHYL-BENZENE | C8H10 | 0.45 |
| 1,4-DIMETHYL CYCLOHEXANE | C8H16 | 0.84 |
| cis-1,3-DIMETHYL CYCLOHEXANE | C8H16 | 0.77 |
| cis/trans-1,3-DIMETHYL-CYCLOHEXANE | C8H16 | 1.12 |
| ETHYLCYCLOHEXANE | C8H16 | 0.87 |
| trans-1,3-DIMETHYL CYCLOHEXANE | C8H16 | 0.18 |
| OCTANE | C8H18 | 0.63 |
| cis-OCTAHYDRO-PENTALENE | C8H14 | 0.16 |
| 1,2,4-TRIMETHYL-BENZENE | C9H12 | 2.59 |
| 1,3,5-TRIMETHYL-BENZENE | C9H12 | 0.54 |
| 1-ETHYL-2-METHYL BENZENE | C9H12 | 0.61 |
| 1,1,3-TRIMETHYL CYCLOHEXANE | C9H18 | 0.52 |
| 1,2,4-TRIMETHYL CYCLOHEXANE | C9H18 | 0.19 |
| 1,2,4-TRIMETHYL-(1.alpha., 2.beta., 4. beta.)-CYCLOHEXANE | C9H18 | 0.28 |
| PROPYLCYCLOHEXANE | C9H18 | 1.35 |
| trans-1-ETHYL-4-METHYL CYCLOHEXANE | C9H18 | 0.41 |
| (1-METHYLETHYL) CYCLOHEXANE and/or 3,6-DIMETHYL OCTANE | C9H18 and/or C10H22 | 1.82 |
| 2,3-DIMETHYL HEPTANE and/or 2,3,5-TRIMETHYL HEXANE | C9H20 | 0.71 |
| 2,5-DIMETHYL HEPTANE | C9H20 | 0.34 |
| 1,2,3,4-TETRAMETHYL-BENZENE | C10H14 | 0.37 |
| 1,2,4,5-TETRAMETHYL BENZENE | C10H14 | 0.81 |
| 1-ETHYL-2,3-DIMETHYL-BENZENE | C10H14 | 1.09 |
| 1-ETHYL-3,5-DIMETHYL-BENZENE | C10H14 | 0.29 |
| ADAMANTANE | C10H16 | 0.57 |
| 4-ETHYL-1,2-DIMETHYL BENZENE and/or 2-ETHYL-1,4-DIMETHYL-BENZENE | C10H18 | 0.74 |
| OCTAHYDR0-5-METHYL-1H-INDENE | C10H18 | 0.79 |
| 1,1,3,4-TETRAMETHYL CYCLOPENTANE | C10H20 | 0.19 |
| BUTYLCYCLOHEXANE | C10H20 | 1.08 |
| cis-1-ETHYL-3-METHYL-CYCLOHEXANE and/or NONANE | C10H20 and/or C9H20 | 1.50 |
| DECANE | C10H22 | 2.13 |
| 3-ETHYL-2-METHYL HePTANE and/or 1-ETHYL-4-(1-METHYLETHENYL) CYCLOHEXANE | C10H22 and/or C10H18 | 1.00 |
| NAPHTHALENE | C10H8 | 1.17 |
| 2-METHYL-NAPHTHALENE | C11H10 | 3.16 |
| (1-METHYLBUTYL)-BENZENE | C11H16 | 1.91 |
| DECAHYDR0-2-METHYL-NAPHTHALENE | C11H20 | 1.49 |
| 4-METHYL-DECANE | C11H24 | 0.62 |
| UNDECANE | C11H24 | 2.11 |
| 1,4-DIMETHYL-NAPHTHALENE and/or 1,2-DIMETHYL-NAPHTHALENE | C12H12 | 0.76 |
| 1,5-DIMETHYL-NAPHTHALENE and/or 1,6-DIMETHYL-NAPHTHALENE and/or 1,7-DIMETHYL-NAPHTHALENE | C12H12 | 1.53 |

TABLE 1-continued

| CRUDE SPECIMEN A | | |
|---|---|---|
| COMPOUND | MOLECULAR FORMULA | APPROXIMATE % OF SPECIMEN |
| 1-ETHYL-NAPHTHALENE and/or 2-ETHYL-NAPHTHALENE | C12H12 | 0.50 |
| 1,3-DIMETHYL-NAPHTHALENE and/or 1,7-DIMETHYL-NAPHTHALEN and/or 2,7-DIMETHYL-NAPHTHALENE | C12H12 | 1.68 |
| 1,3-DIMETHYL-ADAMANTANE | C12H20 | 0.54 |
| HEXYL-CYCLOHEXANE | C12H24 | 0.40 |
| (4-METHYLPENTYL)-CYCLOHEXANE and/or PENTYL-CYCLOHEXANE | C12H24 and/or C11H22 | 0.90 |
| 3,4-DIMETHYL-DECANE | C12H26 | 0.24 |
| DODECANE | C12H26 | 2.43 |
| 1-METHYL-2-PROPYL-CYCLOHEXANE | C12H26O | 0.65 |
| 2-BUTYL-1-0CTANOL | C12H26O | 0.65 |
| 2-METHYL-1,1'-BIPHENYL and/or 3-METHYL-1,1'-BIPHENYL and/or 4-METHYL-1,1'-BIPHENYL | C13H12 | 0.43 |
| 1,4,6-TRIMETHYL-NAPHTHALENE and/or 2,3,6-TRIMETHYL-NAPHTHALENE | C13H14 | 1.00 |
| 1,6,7-TRIMETHYL-NAPHTHALENE and/or 2,3,6-TRIMETHYL-NAPHTHALENE | C13H14 | 0.31 |
| 2-(1-METHYLETHYL)-NAPHTHALENE | C13H16 | 0.42 |
| 1-PENTYL-2-PROPYL-CYCLOPENTANE | C13H26 | 0.49 |
| 2,6-DIMETHYL2,5-DIMETHYL-UNDECANE and/or -UNDECANE | C13H28 | 2.07 |
| 2,6,8-TRIMETHYL-DECANE and/or 2,7,10-TRIMETHYL-DECANE | C13H28 | 1.56 |
| 5-PROPYL-DECANE | C13H28 | 0.58 |
| TRIDECANE | C13H28 | 1.73 |
| 2,3,6-TRIMETHYL-DECANE and/or 2,4,6-TRIMETHYL-DECANE | C13H28 | 0.28 |
| 1-METHYL-9H-FLUORENE and/or 2-METHYL-9H-FLUORINE and/or 4-METHYL-9H-FLUORENE | C14H12 | 0.40 |
| 9-METHYLENE-9H-FLUORENE and/or ANTHRACENE | C14H20 | 0.30 |
| OCTYL-CYCLOHEXANE and/or 1,1'-(1,4-BUTANEDIYL)-CYCLOHEXANE | C14H28 and/or C16H30 | 0.76 |
| TETRADECANE | C14H30 | 1.67 |
| DECAHYDR0-4,4,8,9,10-PENTAMETHYL-NAPHTHALENE | C15H28 | 0.99 |
| CYCLOPENTADECANE | C15H30 | 0.75 |
| 2,6,10-TRIMETHYL-DODECANE and/or 2,7,10-TRIMETHYL-DODECANE | C15H32 | 1.79 |
| PENTADECANE | C15H32 | 1.42 |
| 2,3-DIMETHYL-PHENANTHRENE and/or 2,?-DIMETHYL-PHENANTHRENE and/or 3,6-DIMETHYL-PHENANTHRENE | C16H14 | 0.20 |
| DECYL-CYCLOHEXANE | C16H32 | 0.29 |
| HEXADECANE | C16H34 | 1.37 |
| HEPTADECANE | C17H36 | 2.92 |
| OCTADECANE | C18H38 | 0.87 |
| NONADECANE | C19H40 | 0.89 |
| 2,6,10,14-TETRAMETHYL-HEXADECANE and/or 2,6,10,14-TETRAMETHYL-HEPTADECANE | C19H40 and/or C20H42 | 2.19 |
| 2,6,10,14-TETRAMETHYL-HEXADECANE | C20H42 | 0.76 |
| 2,6,11,15-TETRAMETHYL-HEXADECANE | C20H42 | 0.78 |
| EICOSANE | C20H42 | 0.73 |
| HENEICOSANE | C21H44 | 0.71 |
| DOCOSANE | C22H46 | 0.59 |
| TRICOSANE | C23H48 | 0.50 |
| TETRACOSANE | C24H5O | 0.44 |
| PENTACOSANE | C25H52 | 0.34 |
| HEXACOSANE | C26H54 | 0.26 |
| HEPTACOSANE | C27H56 | 0.17 |
| OCTACOSANE | C28H58 | |
| NONACOSANE | C29H60 | |
| TRIADECANE | C30H62 | |
| HENTRIACONTANE | C31H64 | |

TABLE 2

CRUDE SPECIMEN B

| COMPOUND | MOLECULAR FORMULA | APPROXIMATE % OF SPECIMEN |
|---|---|---|
| METHYLCYCLOHEXANE | C7H14 | 0.45 |
| HEPTANE | C7H16 | 1.15 |
| 1,2-DIMETHYL-BENZENE | C8H10 | 0.56 |
| 1,3-DIMETHYL-BENZENE and/or 1,4-DIMETHYL-BENZENE | C8H10 | 0.48 |
| 1,3-DIMETHYL-CYCLOHEXANE | C8H16 | 0.32 |
| ETHYL-CYCLOHEXANE | CBH16 | 0.90 |
| PROPYL-CYCLOHEXANE | C8H16 | 0.18 |
| 2-METHYL-HEPTANE | C8H18 | 1.54 |
| 3-METHYL-HEPTANE | C8H18 | 1.08 |
| OCTANE | C8H18 | 3.91 |
| 1,3,5-TRIMETHYL-BENZENE and/or 1,2,3-TRIMETHYL-BENZENE and/or 1,2,4-TRIMETHYL-BENZENE | C9H12 | 0.74 |
| 1,3,5-TRIMETHYL-BENZENE and/or 1,2,4-TRIMETHYL-BENZENE | C9H12 | 0.41 |
| 1,3,5-TRIMETHYL-BENZENE and/or 1-ETHYL-3-METHYL-BENZENE | C9H12 | 0.64 |
| 1-ETHYL-2-METHYL-BENZENE and/or 1-ETHYL-3-METHYL-BENZENE | C9H12 | 0.87 |
| 1,1,3-TRIMETHYL-CYCLOHEXANE | C9H18 | 0.29 |
| 1-METHYL-2-PROPYL-CYCLOPENTANE | C9H18 | 0.38 |
| 2,3-DIMETHYL-HEPTANE | C9H20 | 0.84 |
| 2,5-DIMETHYL-HEPTANE and/or 3,5-DIMETHYL-HEPTANE | C9H20 | 0.56 |
| 2,6-DIMETHYL-HEPTANE | C9H20 | 0.61 |
| 2-METHYL-OCTANE | C9H20 | 2.12 |
| 3-METHYL-OCTANE | C9H20 | 1.56 |
| 4-METHYL-OCTANE | C9H20 | 0.20 |
| NONANE | C9H20 | 5.74 |
| 1-ETHYL-2,3-DIMETHYL-BENZENE and/or 2-ETHYL-1,3-DIMETHYL-BENZENE and/or 4-ETHYL-1,2-DIMETHYL-BENZENE | C10H14 | 0.67 |
| 1-ETHYL-3,5-DIMETHYL-BENZENE and/or 2-ETHYL-1,4-DIMETHYL-BENZENE and/or 1-ETHYL-2,3-DIMETHYL-BENZENE | C10H14 | 0.30 |
| 1-METHYL-2-PROPYL-BENZENE and/or 1-METHYL-4-PROPYL-BENZENE | C10H14 | 0.27 |
| 2,6-DIMETHYL-OCTANE and/or 3,6-DIMETHYL-OCTANE | C10H22 | 0.95 |
| 2-METHYL-NONANE | C10H22 | 1.32 |
| 3-ETHYL-2-METHYL-HEPTANE | C10H22 | 2.29 |
| 3-ETHYL-2-METHYL-HEPTANE | C10H22 | 1.36 |
| 3-METHYL-NONANE | C10H22 | 1.61 |
| 4-METHYL-NONANE | C10H22 | 0.83 |
| 4-METHYL-NONANE | C10H22 | 0.85 |
| 5-METHYL-NONANE | C10H22 | 0.30 |
| DECANE | C10H22 | 5.74 |
| NAPHTHALENE | C10HS | 0.23 |
| 1-METHYL-NAPHTHALENE and/or 2-METHYL-NAPHTHALENE | C11H10 | 0.27 |
| 2,4-DIETHYL-1-METHYL-BENZENE | C11H16 | 0.33 |
| 2-METHYL-DECANE | C11H24 | 1.04 |
| 3-METHYL-DECANE | C11H24 | 1.25 |
| 4-METHYL-DECANE | C11H24 | 0.88 |
| 4-METHYL-DECANE | C11H24 | 0.67 |
| 5-METHYL-DECANE | C11H24 | 0.68 |
| UNDECANE | C11H24 | 5.44 |
| 2,7-DIMETHYL-NAPHTHALENE | C12H12 | 0.46 |
| DODECANE | C12H26 | 4.41 |
| 3-METHYL-UNDECANE and/or 1-ETHYL-2,3-DIMETHYL BENZENE | C12H26 and/or C10H14 | 1.12 |
| 1,6,7-TRIMETHYL-NAPHTHALENE and/or 2,3,6-TRIMETHYL-NAPHTHALENE | C13H14 | 0.14 |
| 2,3,4-TRIMETHYL-DECANE and/or 4-METHYL-DODECANE and/or 4,8-D!METHYL-UNDECANE | C13H28 | 0.61 |
| 2,3,5-TRIMETHYL-DECANE | C13H28 | 0.48 |
| 2,3-DIMETHYL-UNDECANE | C13H28 | 0.26 |
| 2,4,6-TRIMETHYL-DECANE | C13H28 | 0.23 |
| 2,6-DIMETHYL-UNDECANE and/or 2,6,7-TRIMETHYL-DECANE | C13H28 | 0.80 |
| 2,8-DIMETHYL-UNDECANE and/or 4,8-DIMETHYL-UNDECANE | C13H28 | 0.62. |
| 2,9-DIMETHYL-UNDECANE and/or 3-METHYL-DODECANE | C13H28 | 0.42 |
| 2-METHYL-DODECANE and/or 2,10-DIMETHYL-UNDECANE | C13H28 | 0.62 |
| 3,3,5-TRIMETHYL-DECANE and/or 3;3,6-TRIMETHYL-DECANE | C13H28 | 0.55 |
| 3,3,8-TRIMETHYL-DECANE and/or 4-METHYL-TRIDECANE and/or .3,3,5-TRIMETHYL-DECANE | C13H28 | 0.49 |
| 3-METHYL-DODECANE | C13H28 | 0.93 |
| 5-(2-METHYLPROPYL)-NONANE | C13H28 | 0.99 |
| TRIDECANE | C13H28 | 3.55 |
| 2-METHYL-TRIDECANE | C14H30 | 0.49 |
| 3-METHYL-TRIDECANE | C14H30 | 0.36 |
| 6-METHYL-TRIDECANE | C14H30 | 0.37 |
| TETRADECANE | C14H30 | 3.01 |
| 4,6-DIMETHYL-DODECANE and/or 4,6-DIMETHYL-UNDECANE | C14H30 and/or C13H28 | 0.31 |
| 2,6,10-TRIMETHYL-DODECANE and/or 2,6,11-TRIMETHYL-DODECANE and/or 2,7,10-TRIMETHYL-DODECANE | C15H32 | 0.37 |
| 2,6,11-TRIMETHYL-DODECANE | C15H32 | 0.60 |
| 2,6,11-TRIMETHYL-DODECANE and/or 2,7,10-TRIMETHYL-DODECANE | C15H32 | 0.32 |
| PENTADECANE | C15H32 | 2.38 |
| 4-METHYL-PENTADECANE and/or 4,11-DIMETHYL-TETRADECANE | C16H34 | 0.22 |
| HEXADECANE | C16H34 | 1.95 |
| HEPTADECANE | C17H36 | 1.95 |
| OCTADECANE | C18H38 | 1.54 |
| NONADECANE | C19H40 | 1.23 |
| 2,6,10,14-TETRAMETHYL-HEXADECANE and/or 2,6,11,15-TETRAMETHYL-HEXADECANE | C20H42 | 0.41 |
| EICOSANE | C20H42 | 1.14 |
| HENEICOSANE | C21H44 | 0.98 |
| DOCOSANE | C22H46 | 0.87 |
| TRICOSANE | C23H48 | 0.74 |
| TETRACOSANE | C24H50 | 0.67 |
| PENTACOSANE | C25H52 | 0.51 |
| HEXACOSANE | C26H54 | 0.56 |
| HEPTACOSANE | C27H56 | 0.39 |
| OCTACOSANE | C28H58 | 0.28 |
| NONACOSANE | C29H60 | 0.24 |
| TRIACONTANE | C30H62 | 0.18 |
| HENTRIACONTANE | C31H64 | |

TABLE 3

CRUDE SPECIMEN C

| COMPOUND | MOLECULAR FORMULA | APPROXIMATE % OF SPECIMEN |
|---|---|---|
| ETHYL-CYCLOPENTANE | C7H14 | 0.17 |
| METHYL-CYCLOHEXANE | C7H14 | 2.93 |
| TOLUENE | C7H8 | 1.77 |
| 1,2-DIMETHYL-BENZENE | C8H10 | 1.27 |
| 1,3-DIMETHYL-BENZENE and/or 1,4-DIMETHYL-BENZENE | C8H10 | 1.27 |
| 3-METHYLENE-HEPTANE | C8H16 | 0.15 |
| 1,2,3-TRIMETHYL-CYCLOPENTANE and/or 1,2,4-TRIMETHYL-CYCLOPENTANE | C8H16 | 0.14 |
| cis-1,3-DIMETHYL-CYCLOHEXANE | C8H16 | 1.86 |

TABLE 3-continued

CRUDE SPECIMEN C

| COMPOUND | MOLECULAR FORMULA | APPROXIMATE % OF SPECIMEN |
|---|---|---|
| ETHYL-CYCLOHEXANE | C8H16 | 1.78 |
| trans-1,2-DIMETHYL-CYCLOHEXANE and/or trans-1,3-DIMETHYL-CYCLOHEXANE | C8H16 | 0.63 |
| trans-1,3-DIMETHYL-CYCLOHEXANE and/or cis-1,4-DIMETHYL-CYCLOHEXANE | C8H16 | 0.64 |
| 2,3-DIMETHYL-HEXANE | C8H18 | 0.21 |
| 2-METHYL-HEPTANE | C8H18 | 2.00 |
| 3-ETHYL-HEXANE | C8H18 | 0.68 |
| 3-METHYL-HEPTANE | C8H18 | 1.31 |
| OCTANE | C8H18 | 4.41 |
| 1,2,3-TRIMETHYL-BENZENE and/or 1,3,5-TRIMETHYL-BENZENE | C9H12 | 1.26 |
| 1,2,3-TRIMETHYL-BENZENE and/or 1,3,5-TRIMETHYL-BENZENE | C9H12 | 1.60 |
| 1-ETHYL-2-METHYL-BENZENE and/or 1-ETHYL-3-METHYL-BENZENE and/or 1-ETHYL-4-METHYL-BENZENE | C9H12 | 1.86 |
| 1-ETHYL-4-METHYL-BENZENE and/or 1-ETHYL-3-METHYL-BENZENE | C9H12 | 0.68 |
| 1,1,3-TRIMETHYL-CYCLOHEXANE | C9H18 | 0.76 |
| PROPYL-CYCLOHEXANE | C9H18 | 1.14 |
| 2,5-DIMETHYL-HEPTANE | C9H20 | 0.83 |
| 2-METHYL-OCTANE | C9H20 | 2.73 |
| 2,6-DIMETHYL-HEPTANE | C9H20 | 0.98 |
| 3-METHYL-OCTANE | C9H20 | 2.13 |
| NONANE | C9H20 | 5.93 |
| 1,4-DIETHYL-BENZENE | C10H14 | 0.22 |
| 1-METHYL-4-(1-METHYLETHYL)-CYCLOHEXANE | C10H20 | 0.28 |
| BUTYL-CYCLOHEXANE | C10H20 | 0.92 |
| BUTYL-CYCLOHEXANE and/or HEXYL-CYCLOHEXANE | C10H20 and/or C12H24 | 0.43 |
| 2,4,6-TRIMETHYL-HEPTANE | C10H22 | 0.22 |
| 2-METHYL-NONANE | C10H22 | 0.98 |
| 3,6-DIMETHYL-OCTANE and/or 2,6-DIMETHYL-OCTANE and/or 3-METHYL-NONANE | C10H22 | 1.27 |
| 3-METHYL-NONANE and/or 3,6-DIMETHYL-OCTANE | C10H22 | 1.25 |
| 4-METHYL-NONANE | C10H22 | 1.98 |
| DECANE | C10H22 | 5.25 |
| 1-METHYL-NAPHTHALENE and/or PENTYL-CYCLOHEXANE | C11H22 | 1.00 |
| 2-METHYL-DECANE | C11H24 | 0.89 |
| 3-METHYL-DECANE | C11H24 | 0.85 |
| 4-METHYL-DECANE | C11H24 | 1.72 |
| UNDECANE | C11H24 | 4.29 |
| 5-METHYL-DECANE and/or 4-ETHYL-HEPTANE | C11H24 and/or C9H20 | 0.58 |
| DODECANE | C12H26 | 3.24 |
| 2,3-DIMETHYLDECANE and/or 4-METHYL-DODECANE and/or 4,8-DIMETHYL-UNDECANE | C12H26 and/or C13H28 | 0.25 |
| 2,10-DIMETHYL-UNDECANE | C13H28 | 0.47 |
| 2,5,6-TRIMETHYL-DECANE | C13H28 | 0.34 |
| 2,6-DIMETHYL-UNDECANE | C13H28 | 1.65 |
| 2,8-DIMETHYL-UNDECANE | C13H28 | 0.39 |
| 5-PROPYL-DECANE | C13H28 | 0.76 |
| TRIDECANE | C13H28 | 2.43 |
| 2-METHYL-TRIDECANE | C14H30 | 0.48 |
| TETRADECANE | C14H30 | 1.93 |
| 2,7,10-TRIMETHYL-DODECANE and/or 2,6,11-TRIMETHYL-DODECANE and/or 3-METHYL-5-PROPYL-NONANE | C15H32 | 0.50 |
| PENTADECANE | C15H32 | 1.32 |
| HEXADECANE | C16H34 | 1.02 |
| HEPTADECANE | C17H36 | 1.35 |
| OCTADECANE | C18H38 | 0.66 |
| NONADECANE | C19H40 | 0.54 |
| 2,6,10,14-TETRAMETHYL-HEXADECANE | C20H42 | 0.29 |
| EICOSANE | C20H42 | 0.45 |
| HENEICOSANE | C21H44 | 0.43 |
| DOCOSANE | C22H46 | 0.36 |
| TRICOSANE | C23H48 | 0.30 |
| TETRACOSANE | C24H50 | 0.29 |
| PENTACOSANE | C25H52 | 0.32 |
| HEXACOSANE | C26H54 | 0.28 |
| HEPTACOSANE | C27H56 | 0.25 |
| OCTACOSANE | C28H58 | 0.22 |
| NONACOSANE | C29H60 | 0.15 |
| TRIACONTANE | C30H62 | 0.10 |
| HENTRIACONTANE | C31H64 | 0.15 |

TABLE 4

CRUDE SPECIMEN D

| COMPOUND | MOLECULAR FORMULA | APPROX. % OF SPECIMEN |
|---|---|---|
| ETHYL-CYCLOPENTANE | C7H14 | 0.17 |
| METHYL-CYCLOHEXANE | C7H14 | 2.93 |
| TOLUENE | C7H8 | 5.57 |
| 1,2-DIMETHYL-BENZENE | C8H10 | 2.39 |
| 1,3-DIMETHYL BENZENE and/or 1,4-DIMETHYL-BENZENE | C8H10 | 4.99 |
| ETHYLBENZENE | C8H10 | 2;10 |
| 1,2,3-TRIMETHYL-CYCLOPENTANE | C8H16 | 0.22 |
| 1,2,4-TRIMETHYL-)1.alpha., 2.beta., 4.alpha.)-CYCLOPENTANE | C8H16 | 0.18 |
| 1,3-DIMETHYL-CYCLOHEXANE | C8H16 | 1;27 |
| ETHYL-CYCLOHEXANE | C8H16 | 1.27 |
| trans-1,2-DIMETHYL-CYCLOHEXANE and/or cis-1,2-DIMETHYL-CYCLOHEXANE and/or trans-1,3-DIMETHYL-CYCLOHEXANE | C8H16 | 0.43 |
| trans-1,4-DIMETHYL-CYCLOHEXANE and/or cis-1,4-DIMETHYL-CYCLOHEXANE | C8H16 | 0.39 |
| 2,3-DIMETHYL-HEXANE and/or 4-METHYL-HEPTANE | CBH18 | 0.25 |
| 2-METHYL-HEPTANE and/or 3-METHYL-HEPTANE and/or 2,5-DIMETHYL-HEXANE | C8H18 | 2.44 |
| OCTANE | C8H18 | 4.77 |
| 1,2,3-TRIMETHYL-BENZENE and/or 1,3,5-TRIMETHYL-BENZENE | C9H12 | 3.t7 |
| 1,3,5-TRIMETHYL-BENZENE and/or 1,2,4-TRIMETHYL-BENZENE | C9H12 | 1.00 |
| 1-ETHYL-3-METHYL-BENZENE and/or 1-ETHYL-2-METHYL-BENZENE | C9H12 | 3.59 |
| 1,1,3-TRIMETHYL-CYCLOHEXANE | C9H18 | 0.39 |
| 1-METHYL-2-PROPYL-CYCLOPENTANE | C9H18 | 0.44 |
| PROPYL-CYCLOHEXANE | C9H18 | 1.11 |
| 2,4-DIMETHYL-HEPTANE | C9H20 | 0.14 |
| 2,5-DIME1HYL-HEPTANE | C9H20 | 0.48 |
| 2,6-DIMETHYL-HEPTANE | C9H20 | 0.69 |
| 2,6-DIMETHYL-HEPTANE and/or 2-METHYL-OCTANE | C9H20 | 1.91 |
| NONANE | C9H20 | 4.45 |
| 1,2,3,4-TETRAHYDRO-NAPHTHALENE | C10H12 | 0.22 |
| 1,2,3,4-TETRAMETHYL-BENZENE | C10H14 | 0.21 |
| 1,2,3,5-TETRAMETHYL-BENZENE and/or 1,2,4,5-TETRAMETHYL-BENZENE | C10H14 | 0.21 |

TABLE 4-continued

CRUDE SPECIMEN D

| COMPOUND | MOLECULAR FORMULA | APPROX. % OF SPECIMEN |
|---|---|---|
| 1-ETHYL-3,5-DIMETHYL-BENZENE and/or 1-ETHYL-2,3-DIMETHYL-BENZENE and/or 4-ETHYL-1,2-DIMETHYL-BENZENE | C10H14 | 0.25 |
| 1-METHYL-2-PROPYL-BENZENE | C10H14 | 0.40 |
| 1-METHYL-3-(1-METHYLETHYL)-BENZENE and/or 1-METHYL-4-(1-METHYLETHYL)-BENZENE | C10H14 | 0.23 |
| 1-METHYL-3-(1-METHYLETHYL)-BENZENE and/or 1-METHYL-2-(1-METHYLETHYL)-BENZENE and/or | C10H14 | 0.31 |
| 1-METHYL-4-(1-METHYLETHYL)-BENZENE and/or 4-ETHYL-1,2-DIMETHYL-BENZENE and/or 1-ETHYL-3,5-DIMETHYL-BENZENE | C10H14 | 0.25 |
| 2-ETHYL-1,4-DIMETHYL-BENZENE and/or 1-ETHYL-2,3-DIMETHYL-BENZENE | C10H14 | 0.48 |
| BUTYL-BENZENE and/or (2-METHYLPROPYL)-BENZENE | C10H14 | 1.11 |
| (2-METHYLBUTYL)-CYCLOPENTANE | C10H20 | 0.21 |
| BUTYL-CYCLOHEXANE and/or UNDECYL-CYCLOHEXANE | C10H20 and/or C17H34 | 0.63 |
| 2,4,6-TRIMETHYL-HEPTANE | C10H22 | 0.20 |
| 2,6-DIMETHYL-HEPTANE and/or 3-METHYL-NONANE | C10H22 | 0.92 |
| 3,4,5-TRIMETHYL-HEPTANE | C10H22 | 0.47 |
| 3-ETHYL-2METHYL-HEPTANE | C10H22 | 0.61 |
| 3-ETHYL-5-METHYL-HEPTANE and/or 5-ETHYL-2-METHYL-HEPTANE | C10H22 | 0.22 |
| 4-METHYL-NONANE and/or 2-METHYL-NONANE | C10H22 | 1.82 |
| DECANE | C10H22 | 3.70 |
| 3-METHYL-NONANE and/or 2,6,11-TRIMETHYL-DODECANE and/or 2,6,7-TRIMETHYL-DECANE | C10H22 and/or C15H32 and/or C13H28 | 0.58 |
| 1-METHYL-3-PROPYL-BENZENE and/or 1-METHYL-4-PROPYL-BENZENE | C10H24 | 1.11 |
| 1-METHYLENE-1H-INDENE and/or AZULENE | C10H8 | 0.30 |
| 2-METHYL-NAPHTHALENE and/or 1-METHYL-NAPHTHALENE | C11H10 | 0.45 |
| 2-METHYL-NAPHTHALENE and/or 1-METHYL-NAPHTHALENE | C11H10 | 0.61 |
| 1,2,3,4-TETRAHYDRO-6-METHYL-NAPHTHALENE and/or 1,2,3,4-TETRAHYDRO-5-METHYL-NAPHTHALENE | C11H14 | 0.18 |
| 1-METHYL-4-(2-METHYLPROPYL)-BENZENE | C11H16 | 0.26 |
| 4-METHYL-DECANE | C11H24 | 0.73 |
| 4-METHYL-DECANE | C11H24 | 0.45 |
| 5-METHYL-DECANE and/or 2,5-DIMETHYL-NONANE | C11H24 | 0.49 |
| UNDECANE | C11H24 | 3.47 |
| 1,3-DIETHYL-5-METHYL-BENZENE | C11H26 | 0.84 |
| 1,2-DIMETHYL-NAPHTHALENE and/or 1,4-DIMETHYL-NAPHTHALENE and/or 2,3-DIMETHYL-NAPHTHALENE | C12H12 | 0.13 |
| 1,7-DIMETHYL-NAPHTHALENE and/or 1,5-DIMETHYL-NAPHTHALENE and/or 2,6-DIMETHYL-NAPHTHALENE | C12H12 | 0.39 |
| 1,8-DIMETHYL-NAPHTHALENE and/or 1,5-DIMETHYL-NAPHTHALENE and/or 1,6-DIMETHYL-NAPHTHALENE | C12H12 | 0.55 |
| 2,7-DIMETHYL-NAPHTHALENE and/or 1,5-DIMETHYL-NAPHTHALENE | C12H12 | 0.60 |
| 2-METHYL-UNDECANE | C12H26 | 0.77 |
| DODECANE | C12H26 | 2.71 |
| 4-METHYL-UNDECANE | C12H26 | 1.37 |
| 3-METHYL-UNDECANE and/or 2-METHYL-DODECANE | C12H26 and/or C13H28 | 0.47 |
| 5,6-DIMETHYL-DECANE and/or 2,4-DIMETHYL-HEPTANE and/or 2,3,5-TRIMETHYL-HEXANE | C12H26 and/or C9H20 | 0.63 |
| 2,3,6-TRIMETHYL-NAPHTHALENE and/or 1,6,7-TRIMETHYL-NAPHTHALENE and/or 2,5,6-TRIMETHYL-DECANE | C13H14 | 0.25 |
| 2,5,6-TRIMETHYL-DECANE | C13H28 | 0.27 |
| 2,6-DIMETHYL-UNDECANE | C13H28 | 0.70 |
| 2-METHYL-4-PROPYL-NONANE | C13H28 | 0.19 |
| 3,6-DIMETHYL-UNDECANE and/or 2,6,8-TRIMETHYL-DECANE | C13H28 | 0.42 |
| 3-METHYL-DODECANE | C13H28 | 0.41 |
| 5-METHYL-DODECANE and/or 5,7-DIMETHYL-UNDECANE and/or 2,4-DIMETHYL-UNDECANE | C13H28 | 0.40 |
| TRIDECANE | C13H28 | 2.27 |
| 4,7-DIMETHYL-UNDECANE and/or 6-ETHYL-2-METHYL-OCTANE | C13H28 and/or C11H24 | 0.21 |
| 1-FLUORO-3-(PHENYLETHENE)-BENZENE and/or 1-FLUORO-4-(2-PHENYLETHENE)-BENZENE | C14H11F | 0.22 |
| 2-METHYL-TRIDECANE | C14H30 | 0.34 |
| 3-METHYL-TRIDECANE | C14H30 | 0.19 |
| 6-METHYL-TRIDECANE | C14H30 | 0.17 |
| TETRADECANE | C14H30 | 1.75 |
| 2,7,10-TRIMETHYL-DODECANE and/or 2,6,10-TRIMETHYL-DODECANE and/or 2,6,11-TRIMETHYL-DODECANE | C15H32 | 0.22 |
| 2,7,10-TRIMETHYL-DODECANE and/or 2,6,11-TRIMETHYL-DODECANE | C15H32 | 0.43 |
| 6-PROPYL-TRIDECANE | C16H34 | 0.19 |
| HEXADECANE | C16H34 | 1.20 |
| HEPTADECANE | C17H36 | 1.27 |
| OCTADECANE | C18H38 | 0.79 |
| NONADECANE | C19H40 | 0.57 |
| 2,6,10,14-TETRAMETHYL-HEXANDECANE | C20H42 | 0.32 |
| EICOSANE | C20H42 | 0.51 |
| HENEICOSANE | C21H44 | 0.42 |
| DOCOSANE | C22H46 | 0.39 |
| TRICOSANE | C23H48 | 0.27 |
| TETRACOSANE | C24H50 | 0.36 |
| PENTACOSANE | C25H52 | 0.27 |
| HEXACOSANE | C26H54 | 0.28 |
| HEPTACOSANE | C27H56 | 0.24 |
| OCTACOSANE | C28H58 | 0.20 |
| NONACOSANE | C29H60 | 0.15 |
| TRIDECANE | C30H62 | 0.16 |
| HENTRIACONTANE | C31H64 | n/a |

The four different oil specimens, A, B, C and D, have been acquired from four different oil reservoirs at locations as diverse as 200 miles. Each was subjected to laboratory analysis by a gas chromatograph with a mass selective detector. The tables provide each detected hydrocarbon compound as described within the analysis, its corresponding molecular formula and the approximate percentage of each compound's component within the specimen. For purposes of this disclosure, each specimen is to be considered less than one drop of oil, with innumerable aggregations required to compose one drop. For purposes of this disclosure, each specimen may be identified as the "fingerprint" of its reservoir source, leading to the location and identification of oil and gas reservoirs at any depth by NMR as seeking their "fingerprint." Extensive field testing has revealed that limited variations of each fingerprint are allowable, resulting in viscosity variations, and are herein disclosed as "familial".

It is known within the industry that various oils were created, or reached maturity, by a combination of organic life sources, including wide varieties of decayed plants and animals, each embodied with wide varieties of original carbon and hydrogen compositions, all submitted to pressurization and heating over eons of time. It is crucial, therefore, that to accurately apply NMR principles to any potential oil or gas reservoir that the person skilled in the art be aware of the origins of life which formulated each and every reservoir being sought. It is further to be understood that in order for each hydrocarbon compound to maintain its homogeneity, or nuclear fingerprint, it must not be in communication with any other type of oil from any source, which would otherwise compromise its fingerprint by the mixture of hydrocarbon compounds. All oil reservoirs must have a seal, called a cap, of dense rock in order to maintain the liquidity of the hydrocarbon compounds in reservoir form, and likewise for natural gas. No matter the thickness of separation at depth within the earth, vertical separation of lateral oil deposits by any thickness of cap rock assures the nuclear fingerprint of each horizon.

The success of locating each and every oil horizon by surface NMR is absolutely assured when properly applied and where enough nuclear energy is present to be emitted to the surface. The basic definition of nuclear magnetic resonance requires a static magnetic field of defined atoms or molecules, each with their own electron spins, which when exposed to an identical external field at vortex, the phenomenon of Larmor frequency generates the motion of spin at the external field on perpendicular investigative devices, commencing with magnetic moment, generation of calculable precession, and ending with relaxation.

The primary magnetic force within oil and gas is hydrogen, which will precess to itself as one atom. However, once that one atom becomes bonded to one or more hydrogen atoms in combination with carbon atoms, entirely new and identifiable hydrocarbon magnetic fields, or fingerprints, are created. As those molecules expand to compounds, each compound assumes its own homogeneous magnetic field, or nuclear fingerprint, and as each hydrocarbon compound expands to dozens of combinations, a new nuclear fingerprint is created with each expansion, with limited allowable familial variations.

By forces of nature, hydrocarbon compounds at various levels within the earth have been subjected to a variety of maturation processes, beginning with their original life forms, to where upon reservoir deposition, a wide variety of hydrocarbon fingerprints have emerged, preserved by eons of time, and resulting in a wide variety of nuclear magnetic possibilities, regardless of the generalized human application of formation names, which often include many different hydrocarbon lenses that may have originated from differing organic matter.

Crude specimens A,B,C and D in Tables 1, 2, 3, and 4 are a small sample of hydrocarbon compounds which have aggregated into singular nuclear magnetic fingerprints. When applied at vortex above their matching nuclear compound in the earth below, at any depth, each precesses at various calculable frequencies to themselves. Specimen A precesses only to itself. Specimen B precesses only to itself. Specimen C precesses only to itself, and specimen D precesses only to itself. Neither will precess in response to the other, assuring geological identity in the earth below. The same rule applies to any suite of specimens obtained and identified as to their source. No matter how many liquid specimens are applied at any one surface location, the radio frequency of each specimen is just as disciplined as radio and television broadcast frequencies.

While each liquid specimen identifies its geological reservoir source from the surface, because natural gas is comprised only of methane (C4 H1), ethane (C2 H6), propane (C3 H8), and butanes (C4 H10), and can exist in any number of geological formations, their precise geological identity cannot be affirmatively verified by surface NMR. However, the existence of natural gas in the earth below and its lateral boundaries can be just as detectible as the earth's liquid hydrocarbons represented in Tables 1, 2, 3 and 4 of this disclosure.

Applying NMR laws, including those of this disclosure, to successful oil and gas exploration and evaluation of existing oil and gas fields, advance calibration must be combined with education as to the geological realities of areas to be explored. The advantage of accurate testing and interpretation results is the success or failure of an expensive drilling operation and/or the intervention on behalf of an exploration company to convince that operator of the absence of petroleum at his proposed site, referred to as "condemnation," or as embodied within this disclosure and claim, the location of faults in the area, which may control deposition and permeability from surface to extreme depths. Attendant advantages are more economically productive oil and gas exploration, narrowing of dry hole losses, and in the case of drilling into highly resistant faults the potential preservation of expensive drilling equipment and the potential prevention of injury to rig crews and loss of life.

Assigning test values upon which to evaluate NMR tests begins with the size and weight of the testing tool, which may not be broadly standardized. For purposes of this disclosure, the test values are based upon tools standardized within the applicant's possession along with standardized molecular specimens. Interpretation of static oil and gas reservoirs, outlining their ambient boundaries, porosity, and permeability, based on their molecular composition, requires mobility for which to establish vortex data points.

Test values disclosed in Table 5 below are based on a working knowledge of geological conditions requisite to a proposed drilling operation or evaluation of an existing oil field. These disclosed values have been tested and compared at various atmospheric conditions which might theoretically influence precession, including seasonal and daytime temperatures, humidity, altitudes, and lunar phases, as well as familial fluid viscosities. The disclosed values are based on an acceptable consortium of interpretations based on actual drilling results, log data, and operator-supplied information derived in twelve U.S. states and have been performed in twenty U.S. states to depths from 500 feet to 30,000 feet and offshore above 1,000 feet of water under standardized pressure conditions. Test values are affected only by the physical laws of NMR and without the interference of ground water, whether fresh or salt, minerals, or non-organic gases. As is known in the science, times of Larmor frequency response are at the speed of light, thus obviating the requirement of speed to surface as a component of interpretation.

TABLE 5

Table of Test Values Interpreted to Reservoir Strength and Production Potential

| Energy Levels | Larmor Strength Interpretation | Porosity Potential | Permeability Potential | Remarks |
|---|---|---|---|---|
| 0 | None | N/A | N/A | No Specimen Response |
| 1-3 | None to Poor | N/A | N/A | Negligible Response |

TABLE 5-continued

Table of Test Values Interpreted to Reservoir Strength and Production Potential

| Energy Levels | Larmor Strength Interpretation | Porosity Potential | Permeability Potential | Remarks |
|---|---|---|---|---|
| 4-6 | Fair | 10%-12% (sand) | <20 Mds. | Not Recommended For Drilling |
|  |  | 5%-8% (limestone) | <20 Mds. | Not Recommended For Drilling |
| 7-8 | Fair to Good | 12%-15% (sand) | >20 Mds. | Stripper Well Potential |
|  |  | 9%-11% (limestone) | >20 Mds. |  |
| 9-10 | Good/Very Good | >15% (sand) | >20 Mds. | Best Initial Production |
|  | Good/Very Good | >11% (limestone) | >20 Mds. | Best Initial Production |
| >10 (Sand) | N/A | N/A | N/A | Free Radical Indicator High Water in Sands |
| >10 (Limestone) | N/A | N/A | N/A | Free Radical Indicator Tight Lime, Little to No Show of Oil |

Table 5 is a table of test values to be derived at test sites demonstrative of nuclear magnetic energy emissions, interpretive reservoir strength per test site, interpretive porosity and permeability potential of sandstone and limestone deposition in milledarcies, disclosure of free radical activity, and an abbreviated "remarks" column upon which to broadly interpret NMR readings on a consulting basis. The column entitled "Energy Levels" is a reflection of spin lattice activity in observation of magnetic force, leading to a prediction of oil saturation at proposed drilling sites and in examination of established oil production. The numbers 0-10 represent increasing levels of magnetic activity by which to interpret fluid concentrations.

The column entitled "Larmor Strength" is an interpretation of those fluid levels as to recovery potentials at a proposed drilling site or within the parameters of the reservoir. The designation "None" indicates the total absence of matching molecular activity in the tested reservoir or of insufficient magnetic spin energy to emit Larmor frequency, indicative of very weak reservoir supply. The designations "Poor", "Fair", "Good" and "Very Good" reveal the increasing magnetic activity at vortex over a proposed drilling site and at scattered locations within a detected reservoir. Most typically, the higher designations (i.e. Good/Very Good) will be within the highest oil saturation, and the lower designations (i.e. Poor/Fair) will be in the pinched out areas of the reservoir or low levels of oil saturation. At vortex over an established oil well, Larmor Strength becomes the basis by which to inventory the remaining recoverable fluids within a reservoir, assuming a straight bore hole.

The column entitled "Porosity Potential" becomes a gauge of porosity in target zones based on fluid concentrations generating greater or lesser magnetic activity. In sandstones, geologists generally recommend porosity of a minimum 12% in self-induced reservoirs and a minimum 7% in limestones. In established oil wells, known porosities as provided by driller logs become a calibration source for NMR activity.

The column entitled "Permeability Potential" is the interpretation of permeability as influenced by oil saturation and comparative permeabilities within the area and as factored by informed geological realities within the area.

The column entitled "Remarks" should accompany any test by which to factor all the test results into predictions and recommendations. In wildcat ventures, all readings are to be considered "best-efforts" by persons skilled in the art.

In the column entitled "Energy Levels," provision is made with the symbol ">10," by which to indicate "Free Radical" (FR) activity within a given formation. There is no such thing as "false readings" in nuclear magnetic resonance. The earth is not a solid rock. Its many diverse layers of rocks are testaments to the many geological ages which in one way or another piled up to what man sees today. Many of those geological layers became the dispersed repositories or were highways for hydrocarbons which matured from decayed life. Oil and gas wells also encounter fresh and/or salt water in many of those layers when drilling to depth. Free radicals are the smallest molecular footprints of oil and/or gas which passed through various rock formations, or have freed themselves from liquid reservoirs in the minutest form, or may be carried as sheen by water. It is known within the science of physics that molecular free radicals are more reactive than fluids and often reveal themselves within an NMR test from the surface as "high readings." They are insufficient to be productive sources of oil, and without proper surface interpretation can lead to false hopes for a highly successful oil well. Experience proves that NMR energy levels in excess of the 10 "energy level" seldom produce a show or odor of oil, and when an FR zone is encountered while drilling, its reading disappears entirely by the release of locked molecular compounds into drilling fluids and to the surface. Free radical readings never show up at established oil wells, and multiple FR readings at proposed drilling sites are strong indicators of low permeability or high water saturations within their various anticipated zones. FR readings occur in almost every NMR test at proposed wildcat locations and many offset locations, because those free molecules have never been released from their locked positions at depth. High readings are tantalizing and very difficult to resist in belief higher readings translate into higher oil saturation. The fact is the opposite is true. Recognizing their potential is one of the most important tools for reliable exploratory NMR testing. Proper understanding and interpretation of this principle leads to a more accurate NMR test, more economically productive oil well, and/or avoidance of dry holes.

Figure 2:
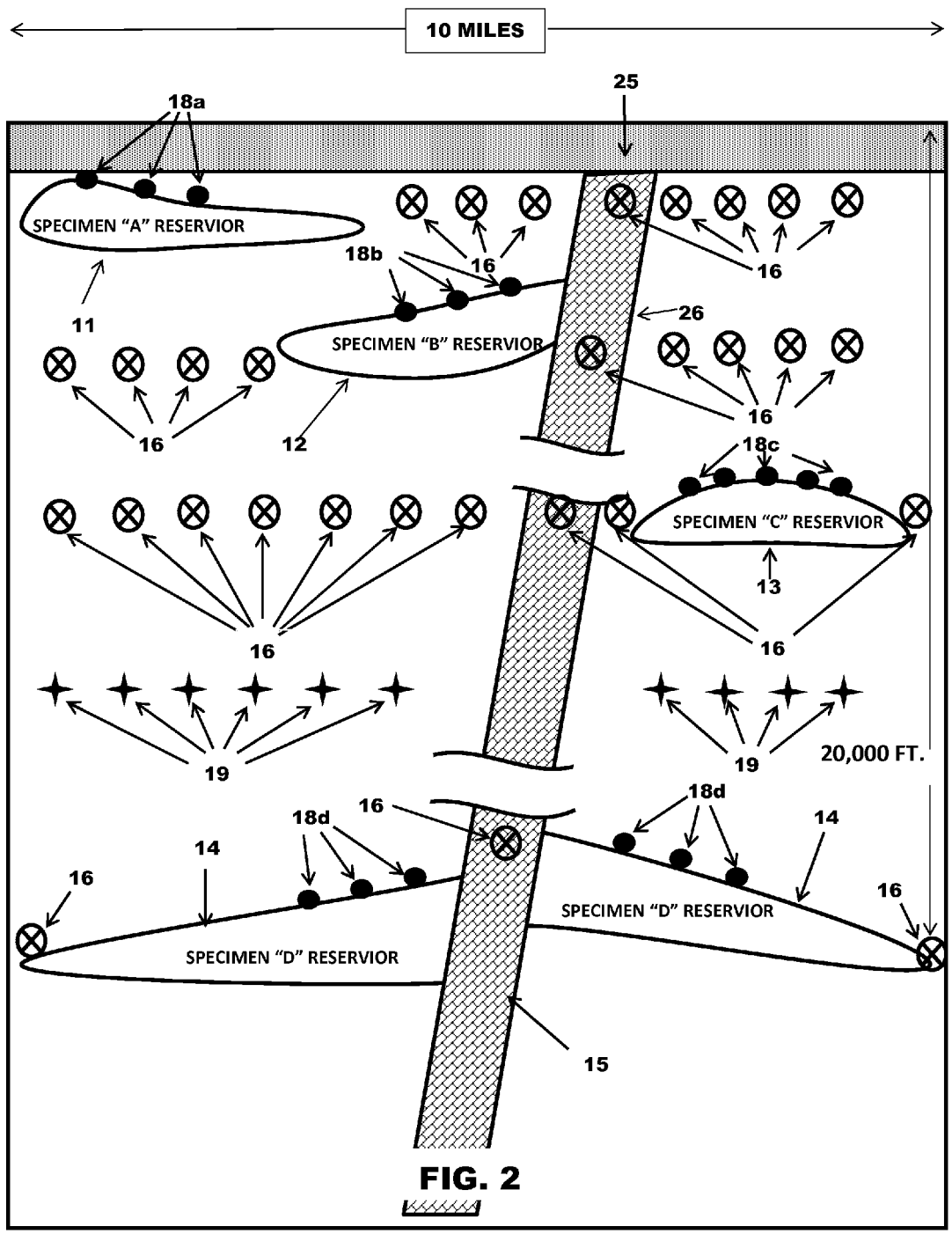
FIG. 2 is a side elevation view in cross-section of the first hypothetical oil and/or gas production area of FIG. 1.

FIG. 1 and FIG. 2 illustrate a first hypothetical one hundred twenty square mile oil and/or gas production area of investigation reflecting the presence of oil reservoirs recognized by specimens A, B, C, and/or D. The view of FIG. 1 is top down, while FIG. 2 is a side view in elevation of the same area. Transversing the field is a theoretical fault 15 unseen to the naked eye beneath a relatively flat surface overlain with sediment 25, but detected by inverse NMR. Test data points 16 are scattered within the block where tests revealed no presence of specimens A, B, C, or D. NMR indicates reservoir A (1,000 feet deep) 11, and reservoir B (5,000 feet deep) 12, overlap on the west side of the fault 15. Reservoir C (10,000 feet deep)

13, is deposited on the east side of the fault 15, while reservoir D (20,000 feet deep) 14, underlies all three established reservoirs. Theoretically all four reservoirs have been unexplored, to where recommended drilling locations 18a, 18b, 18c, 18d, respectively, are staked using NMR with declining values indicating the lateral, non-producible boundaries 17a, 17b, 17c, 17d of each respective reservoir 11, 12, 13, 14. Free radical indicators 19 are scattered within the area.

The advantages to the oil companies having employed NMR technology to analyze their leases is to find oil they did not know existed, drill only in the areas of highest production potential, avoid the less productive boundaries 17a, 17b, 17c, 17d of the reservoirs 11, 12, 13 and 14, avoid the fault 15, completely ignore areas where no potential exists at all 16, and be aware of the fault 15 and its effects on drilling potential. For purposes of this disclosure, test data points 16 are indicated at random intervals in search of reservoirs which answer by NMR to specimens A, B, C, and D. However, when micro-testing potential oil reservoirs for their lateral boundaries 17, internal oil concentrations, porosity and permeability potentials, NMR data points become much tighter and more resolute. A hypothetical free radical zone 19 is also indicated by which to illustrate a condition which may occur within any test block in any oil formation.

Figure 3:
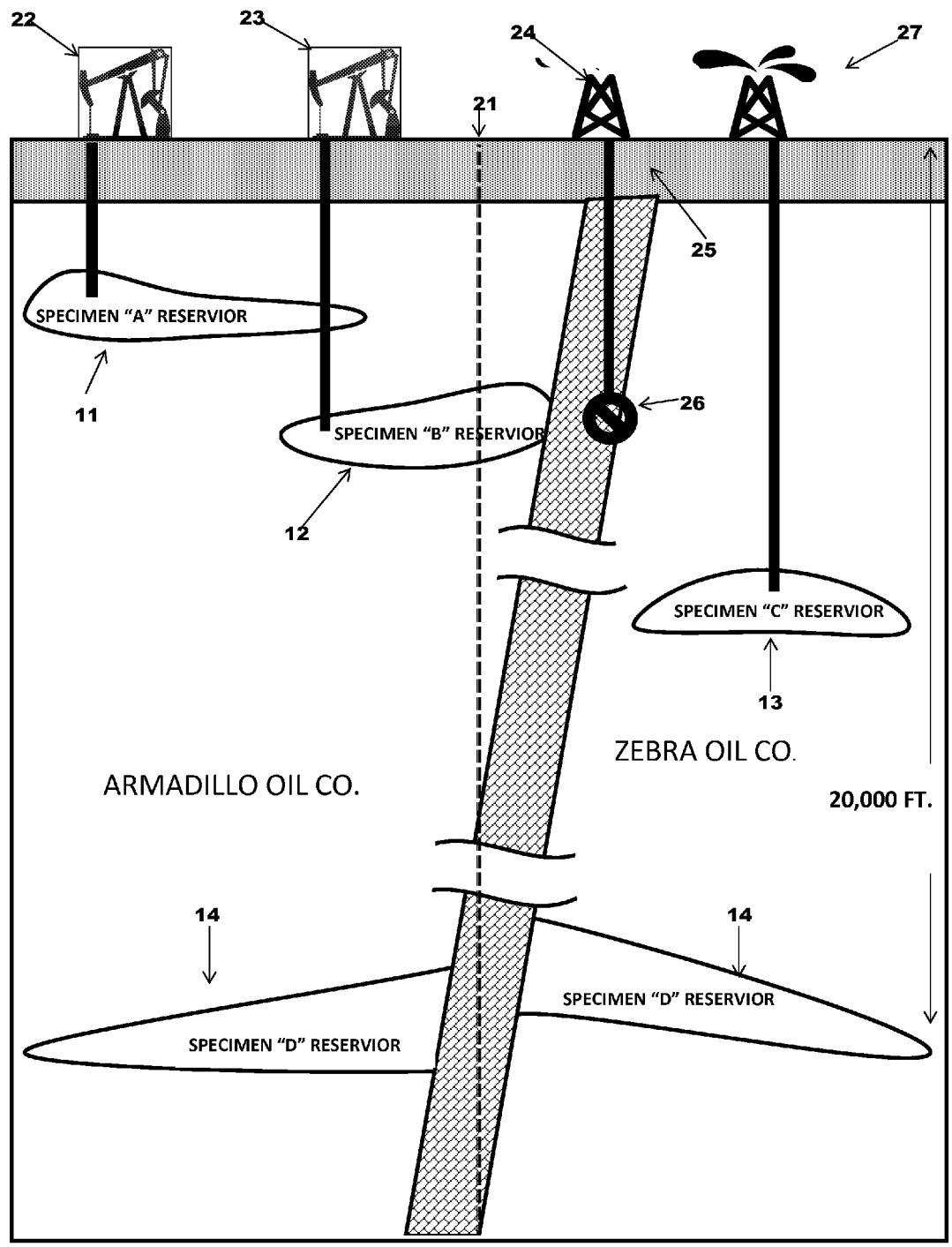
FIG. 3 is a side elevation view in cross-section of the hypothetical oil and/or gas production area of FIG. 1 and FIG. 2, showing multiple drilling operations of two different hypothetical oil operators separated by a dividing property line.

FIG. 3 is a hypothetical view of the existing production area of FIG. 1 and FIG. 2, shown here as owned by fictional oil operators, Armadillo Oil Company and Zebra Oil Company divided by property line 21. Fictional operator Armadillo Oil Company drills two wells 22, 23 on the west side of this illustration without the assistance of NMR. His first well 22 encounters and produces oil from reservoir A 11 at 1,000 feet. In his second attempt, Armadillo encounters Reservoir A 11 on its edge 17, which is non-producible or burdened with copious amounts of salt water, and continues to 5,000 feet, where he encounters reservoir B 12, and produces it at his second well 23. Because he did not know of the existence of the greater and more prolific reservoir D 14 below him at 20,000 feet, he did not drill it. Without an NMR test, the reservoir D 14 might lie unproduced for many years on his lease.

Zebra Oil Company attempts to drill a well by which to encounter the same two reservoirs 11, 12 being produced by competitor Armadillo Oil Company. Zebra's first well 24 is drilled within the nearest legal location from the property line 21 to encounter Armadillo's reservoir A 11 and reservoir B 12, but Zebra misses both and drills into the unseen fault 15, because it was covered by tertiary sediment 25, resulting in a dry hole 26. Zebra moves to the east and attempts once again to encounter reservoir A 11 and reservoir B 12, but no oil is found in those potential reservoirs. Zebra continues to 10,000 feet and encounters reservoir C 13, known to produce in the area, and begins production at its second well 27. Like Armadillo, Zebra still does not know the greater and more prolific reservoir D 14 exists at 20,000 feet. NMR testing eventually reveals to both operators the analysis of their reservoirs and greater potential.

Both scenarios demonstrated in FIG. 3 exist all over the world and have been repeated millions of times for 150 years. In both scenarios, NMR would have prevented both operators from drilling dry holes, drilling marginal wells, hitting a fault, and potentially would have influenced the operators to drill more economically to depths with the highest production potential of oil, with the best porosity and permeability, and to more prolific reservoirs at deeper depths. In these cases, NMR would both save operators and their investors from wasting money and direct the operators and their investors to higher returns.

Figure 4:
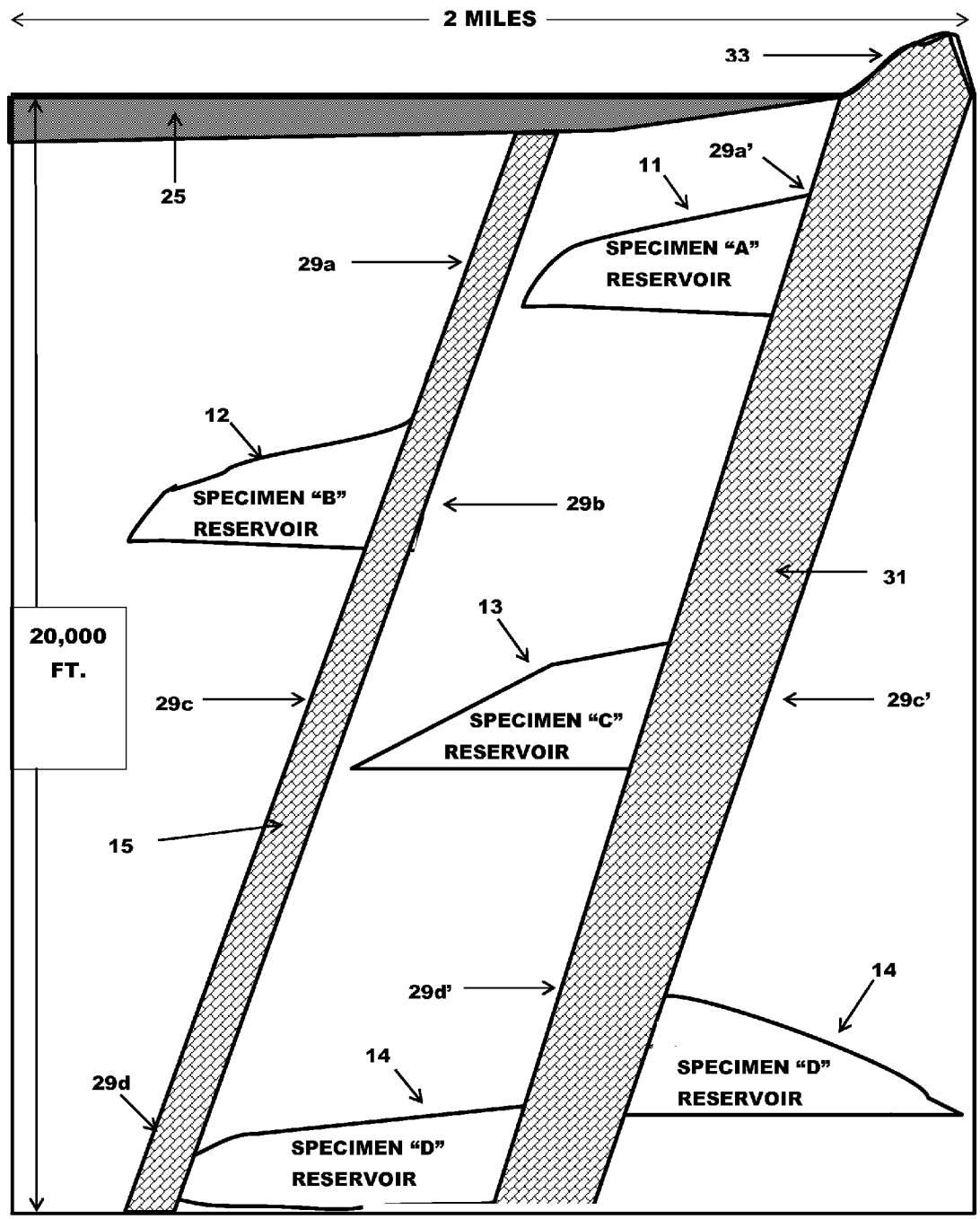
FIG. 4 is a side elevation view in cross-section of a second hypothetical oil and/or gas production area with an illustration of faults which permeate the earth both in obvious outcrops and unseen locales covered with tertiary sediment.
Figure 5:
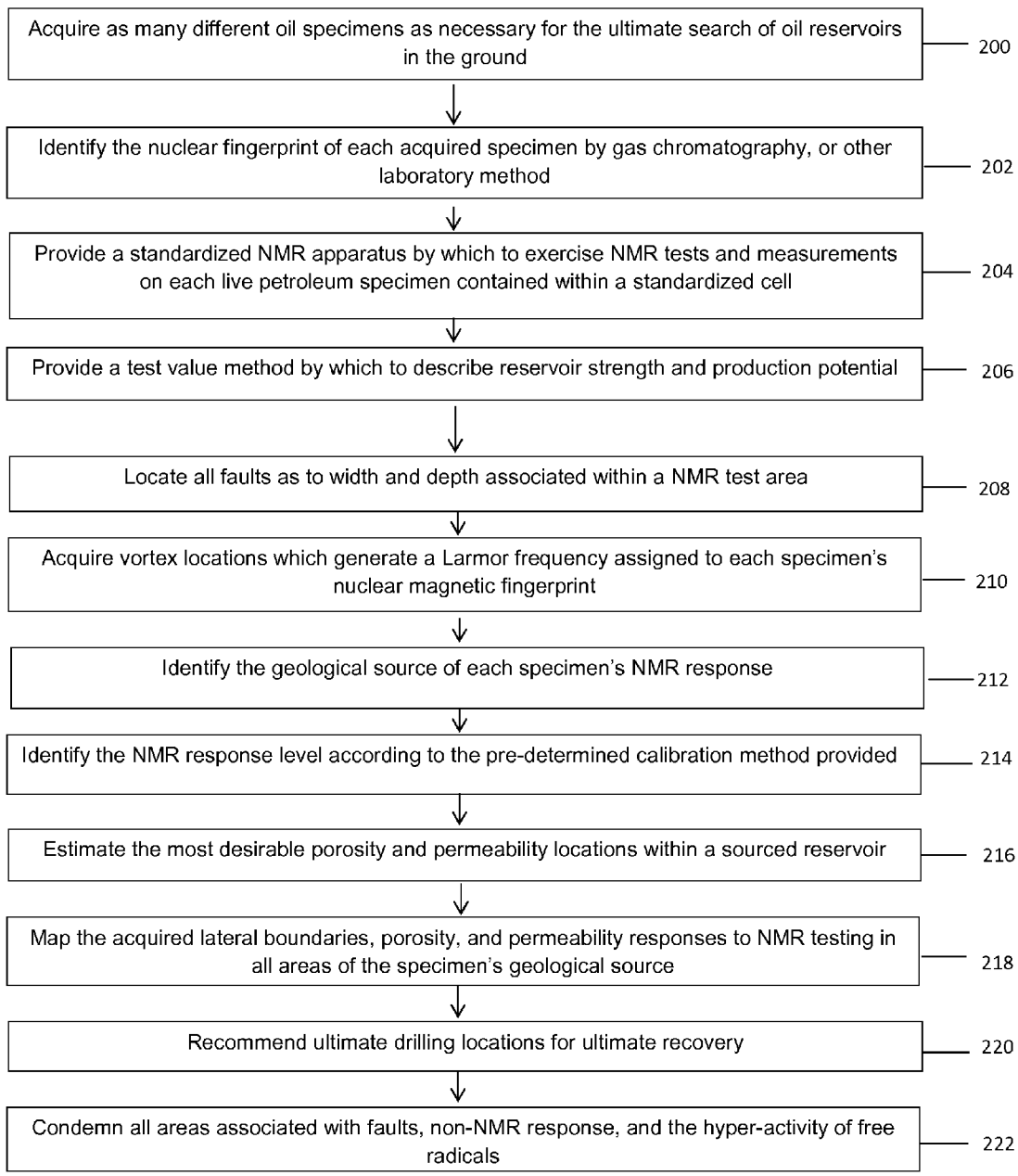
FIG. 5 is a flow-chart diagram demonstrating the steps to be taken for preparation, performance, interpretation, and mapping the results of NMR evaluation of virgin fields, existing fields, faults and free radicals, and/or the condemnation of areas non-responsive to NMR testing.

FIG. 4 illustrates the ability to locate faults at any depth in oil and gas production areas, using NMR. Faults are displacements of the earth's crust caused by conflicting plate pressures over eons of time, often resulting in earthquakes, and pervade every area of the world, including oil country. Faults are seen in many shapes and sizes. They can run for hundreds of miles in any direction, and like rivers, are often linked to smaller, tributary faults, called "finger" faults. Most major faults reveal themselves at the surface as mountainous or hilly outcrops 33, are visible from the air and to the naked eye, but many unseen faults are covered by tertiary sediment 25 and not known until encountered by drilling. Most major faults have been mapped, are often displayed on geologists' isopach contour maps, where known, and can be detected underground by seismics. Faults are always a major consideration to oil and gas exploration companies, because on one side they can provide prolific reservoirs, and can tighten formations on the other, due to pressure.

Many of the best oil and gas reservoirs are found on one side of a fault only to be severely pinched on the other side, resulting in dry holes. Drilling into faults can be dangerous to equipment and have been known to jettison drill pipe to the surface, raining down on equipment and workers. Oil can be found in faults, but commercial recovery of oil is a high risk. Many wells drilled into faults eventually are converted to water injection wells, but observation at some of those locations can reveal seeps of oil and salt water to the surface draining into creeks, having been rejected by the unseen, underlying displaced rocks. Many minor faults are never mapped, and their directional paths and depths remain a mystery until encountered multiple times by both major and minor drilling operators.

The function of detecting faults by NMR is inverse oscillation caused by the inversion of vortex paths. Perpendicular horizontal planes are required by which to achieve vortex and Larmor frequency, resulting in counterclockwise oscillation of a specimen tool. When faulting occurs, the displaced, angular rock formations resist typical transverse magnetization. When met by nuclei within any fluid specimen, inverse magnetism reveals rock displacement at depth equal to the respective specimen's source 29a, 29b, 29c, 29d as shown in FIG. 4.

Application of a full suite of specimens eventually reveals the depth of the fault according to geological age, as well as its depositional direction. In FIG. 4, two faults are represented. While fault 15 is the same fault represented in FIG. 1 and FIG. 2, covered by tertiary sediment 25 and unseen to the naked eye beneath a relatively flat surface, fault 31 to the east has risen above the surface as a hillside or mountain 29, is visible, and probably mapped. While geologists might determine the age rocks contained within that fault, it's earth angle at 1,000 feet, 5,000 feet, 10,000 feet, or 20,000 feet are unknown until it has been penetrated by drilling or detected by seismics or NMR. Thus, its effect on oil deposition remains unclear. Because many areas of oil country have not been seismographically tested, NMR becomes an easy and totally uninvasive method of evaluating faults 15 and 31.

At both faults 15 and 31, all four specimens A, B, C, D are applied in search of any faulting which might exist in the area. Each results in inverse oscillation at points 29a, 29b, 29c, 29d represented by each respective reservoir when tested. Upon further evaluation, reservoir A 11 is found to be trapped against fault 31 at 1,000 feet with highly favorable porosity and permeability. Reservoir C 13 is found at 10,000 feet, while reservoir D 14 is found to be upthrust and downthrown by the fault 31, subject to evaluation of oil saturation, porosity, and permeability on both sides.

All four specimens A, B, C, D are likewise applied by which to locate fault 15 to the west. Inverse reactions occur at points 29a, 29b, 29c, 29d represented by the depth of each of the four respective reservoirs 11, 12, 13, 14 along the fault 15. When NMR is applied using specimen A, no oil is found against the fault 15 at 1,000 feet, but inverse NMR detects the fault at that point 29a. The same holds true for specimen C at 10,000 feet where inverse NMR detects the fault at point 29c, and for specimen D at 20,000 feet where inverse NMR detects the fault at point 29d. In contrast, NMR does positively locate reservoir B 12 that is located against the fault 15 at 5,000 feet. On the east side of the fault 15, specimen D oil is found trapped against the fault.

Advantages of this disclosure are the ability to locate any fault in the earth at any depth affecting oil and gas exploration, thereby providing drillers information by which to avoid drilling into faults, either to loss of their money and equipment, injury and/or loss of life to rig workers, or being falsely tantalized by oil shows within a fault, the ability to locate oil best trapped against a fault with highest recovery potential, the ability to interpret pinched areas on opposite sides of faults, indicating less production potential, the ability to locate oil at depths below minor faults, and the contribution of mapping unseen faults for future geological consideration.

The foregoing is provided for purposes of illustrating, explaining, and describing embodiments of the present invention. The specific components and order of the steps listed above, while preferred is not necessarily required. Further modifications and adaptation to these embodiments will be apparent to those skilled in the art and may be made without departing from the scope or spirit of the invention.

I claim:

1. A method for detecting subterranean reservoirs of oil and/or gas comprising the steps of:
    obtaining a specimen of oil having a known composition of elements and compounds;
    providing a standardized NMR apparatus having a standardized cell;
    introducing a molecular amount of said specimen in said standardized cell;
    orienting the standardized cell proximal and perpendicular to the earth;
    scanning at or near the surface of the earth with said standardized cell containing said specimen until said standardized cell precesses;
    assigning test values upon which to evaluate the precession of the standardized cell; and
    determining the presence or absence of oil in the ground based on said assigned test values and the precession of the standardized cell.

2. The method of claim 1 further comprising the step of obtaining a nuclear magnetic fingerprint of the specimen by analyzing said specimen by molecular fluid property analysis.

3. The method of claim 2 wherein the nuclear magnetic fingerprint of the specimen is obtained by gas chromatography.

4. The method of claim 2 wherein the nuclear magnetic fingerprint of the specimen is obtained by mass selection.

5. The method of claim 1 wherein the step of obtaining a specimen of oil comprises obtaining a plurality of oil specimens from a plurality of oil reservoirs.

6. The method of claim 1 wherein the step of assigning test values includes the steps of:
    a. Assigning an energy level value based on a reflection of spin lattice activity in observation of magnetic force;
    b. Assigning a Larmor strength value based on the level of matching molecular activity at vortex;
    c. Assigning a porosity potential as a gauge of porosity in the earth based on fluid concentrations generating greater or lesser magnetic activity; and
    d. Assigning a permeability potential based on oil saturation and comparative permeabilities within the area and as factored by informed geological realities within the area.

7. The method of claim 6 wherein the step of determining the presence or absence of oil comprises comparison of the energy level value, Larmor strength value, porosity potential and permeability potential.

8. The method of claim 7 further comprising the step of determining the presence of free radicals in the earth.

9. The method of claim 8 wherein the presence of free radicals is determined by high energy level readings.

10. The method of claim 1 further comprising the step of detecting and locating all faults as to width and depth associated within the test area.

11. The method of claim 10 wherein the step of detecting and locating all faults comprises the step of observing inverse oscillation of the standardized cell containing the oil specimen as it is passed over the earth.

12. The method of claim 11 comprising the step of repeating the step of detecting and locating all faults using a plurality of oil specimens from a plurality of oil reservoirs.

13. The method of claim 12 comprising the step of mapping the acquired lateral boundaries, porosity, and permeability responses to NMR testing in all ares of the geological source of the specimen.

14. The method of claim 13 comprising the step of recommending ultimate drilling locations for ultimate recovery of oil.

15. The method of claim 14 comprising the step of condemning all areas associated with faults, non-NMR response, and the hyper activity of free radicals.

* * * * *